US006120472A

United States Patent [19]
Singer, Jr.

[11] Patent Number: 6,120,472
[45] Date of Patent: Sep. 19, 2000

[54] FOREARM SPLINT SYSTEM FOR TREATMENT AND PREVENTION OF CARPAL TUNNEL SYNDROME AND OTHER CUMULATIVE TRAUMA DISORDERS

[76] Inventor: Richard F. Singer, Jr., 7312 Gold Ring Ter., Derwood, Md. 20855

[21] Appl. No.: 09/186,658

[22] Filed: Nov. 6, 1998

[51] Int. Cl.[7] ...................................................... A61F 13/00
[52] U.S. Cl. .................................. 602/64; 602/20; 602/21
[58] Field of Search .................................. 602/20, 21, 60, 602/61, 62, 63, 64, 22; 128/877–880; 2/162, 170, 455, 16, 159, 161.1, 161.6, 161.7

[56] References Cited

U.S. PATENT DOCUMENTS

| | | |
|---|---|---|
| Re. 34,627 | 5/1994 | Davini . |
| 923,217 | 6/1909 | Tyrell ......................................... 602/64 |
| 4,047,250 | 9/1977 | Norman . |
| 4,048,991 | 9/1977 | Marx . |
| 4,183,098 | 1/1980 | Knowles, Jr. . |
| 4,309,991 | 1/1982 | DeMarco . |
| 4,584,993 | 4/1986 | Nelson . |
| 4,716,892 | 1/1988 | Brunswick . |
| 4,854,309 | 8/1989 | Elsey . |
| 4,883,073 | 11/1989 | Aziz . |
| 4,899,763 | 2/1990 | Sebastian et al. . |
| 4,966,137 | 10/1990 | Davini ....................................... 602/21 |

(List continued on next page.)

FOREIGN PATENT DOCUMENTS 3838564  5/1990  Germany ............................. 602/64 X

OTHER PUBLICATIONS

Multiple Authors, Cumulative Trauma Disorders in the Workplace, Sep., 1995, pp. vi, 44,124,U.S. Department of Health and Human Services, Public Health Services, Centers for Disease Control and Prevention, National Institute for Occupational Safety and Health Education and Information Division, 4676 Columbia Parkway, Cincinnati, Ohio 45226.

Do wrist braces/splints help or harm workers? CTD News, Jul.Aug. 93, vol. 2, No. 7, CTD News, Inc. and the Center for Information on Cumulative Trauma Disorders, PO Box 239, Haverford, PA 19041.

David T. Burke, M D. et al. Splinting for Carpal Tunnel Syndrome: In Search of The Optimal Angle, Archives of Physical Medicine & Rehabilitation vol. 75, Nov. 1994, American Congress of Rehabilitation Medicine and the American Academy of Physical Medicine and REhabilitation pp. 1241–1244.

Robert M. Szabo, M.D. et al. Carpal Tunnel Syndrome pp. 103–109 Orthopedic Clinics of North America, vol. 23, No. 1, Jan. 1992.

Edwin M Smith, M D et al. Carpal Tunnel Syndrome: Contribution of Flexor Tendons, pp. 379–385, Archives of Physical Medicine & Rehabilitation, vol. 58, Sep. 1977.

Craig A. Banta, M.D A Prospective, Nonrandomized Study of Iontophoresis, Wrist Splinting, and Antiinflammatory Medication in the Treatment of Early–Mild Carpal Tunnel Syndrome, pp. 166–168, Journal of Occupational Medicine, vol. 36, No. 2, Feb. 1994, American College of Occupational and Environmental Medicine.

Shiro Tanaka et al. A conceptual quantitative model for prevention of work–related carpal tunnel syndrome (CTS), pp. 181–193, International Journal of Industrial Ergonomics, II(1993), Elsevier Science Publishers, B.V.

David Rempel, M. D et al. The Effect of Wearing a Flexible Wrist Splint on Carpal Tunnel Pressure During Repetitive Hand Activity, pp. 106–110, The Journal of Hand Surgery, vol. 19A, No. 1, Jan. 1994, Churchill Livingstone Inc.

*Primary Examiner*—Kim M. Lee
*Attorney, Agent, or Firm*—Dowell & Dowell, P.C.

[57] ABSTRACT

A forearm splint system and method of use for treatment and prevention of carpal tunnel syndrome and other cumulative trauma disorders including adjustable tensioning means causes rotation of two curved, semi-rigid pieces of material within the splint system. The rotation causes rotation and repositioning of the distal radius and ulna bones, resulting in widening of the carpal tunnel, decreased compression of the median nerve, and improved frictionless gliding and sliding of the flexor tendons.

12 Claims, 3 Drawing Sheets

U.S. PATENT DOCUMENTS

| | | |
|---|---|---|
| 4,991,234 | 2/1991 | Greenberg . |
| 5,014,689 | 5/1991 | Meunchen et al. . |
| 5,160,314 | 11/1992 | Peters . |
| 5,256,136 | 10/1993 | Sucher . |
| 5,267,943 | 12/1993 | Dancyger . |
| 5,279,545 | 1/1994 | Reese, Sr. .................. 602/21 |
| 5,385,537 | 1/1995 | Davini . |
| 5,397,296 | 3/1995 | Sydor et al. . |
| 5,409,451 | 4/1995 | Daneman . |
| 5,413,553 | 5/1995 | Downes . |
| 5,415,624 | 5/1995 | Williams .............................. 602/64 X |
| 5,417,645 | 5/1995 | Lemmen . |
| 5,441,058 | 8/1995 | Fareed . |
| 5,466,215 | 11/1995 | Lair et al. . |
| 5,468,220 | 11/1995 | Sucher . |
| 5,478,306 | 12/1995 | Stoner . |
| 5,484,392 | 1/1996 | Sydor et al. . |
| 5,513,657 | 5/1996 | Nelson . |
| 5,538,501 | 7/1996 | Caswell . |
| 5,672,151 | 9/1997 | Calderon-Garciduenas .......... 602/64 X |
| 5,728,059 | 3/1998 | Wiesmann et al. ...................... 602/64 |
| 5,746,707 | 5/1998 | Eck . |
| 5,759,166 | 6/1998 | Nelson et al. ............................ 602/64 |
| 5,766,141 | 6/1998 | Gould . |
| 5,769,808 | 6/1998 | Matthijs et al. . |
| 5,810,753 | 9/1998 | Eberbach ................... 602/21 |
| 5,921,949 | 7/1999 | Dray ......................... 602/64 |

FOREARM SPLINT SYSTEM FOR TREATMENT AND PREVENTION OF CARPAL TUNNEL SYNDROME AND OTHER CUMULATIVE TRAUMA DISORDERS

BACKGROUND OF THE INVENTION

A group of conditions that has presented a challenge to both health care providers and ergonomists are the upper extremity cumulative trauma disorders. This includes carpal tunnel syndrome, DeQuervain's tenosynovitis, cubital tunnel syndrome, Guyon's tunnel syndrome, intersection syndrome, and repetitive strain injury. There has been a steady increase in the number of reported cases of cumulative trauma disorders over the past several years. This is in part due to the increased awareness of these conditions among the general public. The increase in cumulative trauma disorders can also be attributed to the growing use of computers, although an individual can develop a cumulative trauma disorder without having used a computer. Manual use of the keyboard and/or mouse requires frequent, highly coordinated use of one's forearms, wrists, hands, fingers and thumbs for accurate data entry. This requires very brief but very frequent contractions of the muscles and their associated tendons. This may prevent adequate relaxation between contractions and lead to the development of cumulative trauma or overuse of these tissues.

The carpal tunnel, and structures therein, are the most frequently effected tissues in upper extremity cumulative trauma disorders. The structures within the carpal tunnel include the finger and thumb flexor tendons, the flexor carpi radialis tendon, the flexor carpi ulnaris tendon and the median nerve. The volar surface, or what may be called the roof of the carpal tunnel, is formed by the flexor retinaculum and the transverse carpal ligament. The dorsal surface, or what may be called the floor of the carpal tunnel, is formed by the pronator quadratus muscle, the distal radioulnar joint, the radiocarpal joint, the triangular fibrocartilage complex, the proximal row of carpal bones and the associated joint capsules and ligaments.

Carpal tunnel syndrome is a compression neuropathy of the median nerve as it passes through the carpal tunnel. The median nerve supplies sensation to the volar, also known as palmar, aspect of the thumb, index, middle finger and the radial (thumbside) half of the ring finger. Symptoms of carpal tunnel syndrome include numbness, tingling, burning sensations and pain. This involves not only the area of innervation described but may also radiate above the wrist into the forearm. Intact sensation to this part of the hand is essential for the coordinated, highly repetitive use of the fingers, thumbs and wrist flexors to operate the computer keyboard and mouse.

The development of carpal tunnel syndrome is caused by excessive pressure on the median nerve within the carpal tunnel. The carpal tunnel is a confined space and any factors that contribute to increasing pressure within the tunnel may contribute to the development of carpal tunnel syndrome. Related cumulative trauma disorders may also develop as one attempts to compensate for this increased pressure and subsequently overuse related muscles and tendons. Normal function of tendons, including the flexor tendons of the fingers and thumbs, requires relatively frictionless gliding and sliding of each tendon independent from neighboring tendons, nerves and ligaments. Overuse of these tendons can lead to inflammatory changes, that is thickening and swelling, of these tendons. Since the volume of the carpal tunnel is limited this leads to increased pressure within the tunnel, thus contributing to the development and/or worsening of carpal tunnel syndrome.

Previously reported treatment for carpal tunnel syndrome and other cumulative trauma disorders has included rest from provocative activities, anti-inflammatory medications, steroid injections, surgery, and/or the use of wrist splints either in a neutral or extended, so called cock-up, wrist position. While these measures often prove to control symptoms temporarily they have proven to be less successful in permanently controlling or relieving symptoms. Neutral or cock-up wrist splints have provided control of symptoms for some people during sleeping hours. However use of these splints during waking hours has proven to be impractical for most people due to the rigid immobilization of the wrist and partial immobilization of the base of the thumb that these splints create. In fact such restricted range of motion of the wrist and thumb may aggravate carpal tunnel syndrome and cumulative trauma disorders due to the abnormal manner in which the finger and thumb flexors and extensors would be forced to function while wearing said splint.

Permanently avoiding provocative activities may also be an impractical solution as it may be a required activity in one's occupation or adversely effect the quality of one's life, for example having to give up a sport, recreational activity or hobby. Surgical resection of the transverse carpal ligament may offer more permanent control of symptoms however there is a period of temporary disability following surgery. Additionally there are inherent risks with any surgical procedure. Also it has been proven to be an expensive method of treatment. Lastly there is a possibility of symptoms returning when one resumes their pre-surgical activities and in some cases more severe symptoms may develop due to post-surgical scar formation in the carpal tunnel.

Other prior art includes a bracelet (U.S. Pat. No. 5,468,220 to Sucher) intended to stretch the transverse carpal ligament to reduce pressure in the carpal tunnel. However it is known that stretching the transverse carpal ligament causes a temporary aggravation of carpal tunnel syndrome symptoms and therefore may not be tolerated by the individual. Additionally the stretch is achieved by three small pads which over an extended period of wearing may cause excessive tissue compression, circulatory congestion and skin irritation. Also the device requires periodic adjustments by a physician which adds inconvenience and cost to the use of said device.

Additional prior art includes a splint system intended to support the carpal tunnel by approximating the radius and ulna toward one another (U.S. Pat. No. 5,385,537 to Davini). This is accomplished in part by a semi-rigid V-shaped brace. However, the contour of the side of one's wrist is not V-shaped, causing this semi-rigid material to protrude from the wearer's wrist on both free ends. This may be impractical to wear during provocative activities due to the fact that it may become entangled in objects near the wearer's hands. This potential for entanglement also poses a safety hazard when the wearer is operating power equipment or machinery while wearing said brace. Additionally the approximation of the radius and ulna may cause excessive compression of the distal radioulnar joint, its' associated cartilage and the closely related triangular fibrocartilage complex.

What is desired and hereby presented is a splint system which does not immobilize the wrist, hand, fingers or thumb. These and other difficulties associated with prior art devices have been avoided in the novel manner by the present invention.

In view of the foregoing, it is therefore a primary object of this invention to provide a forearm splint system which achieves improved successful treatment of carpal tunnel syndrome and other cumulative trauma disorders.

A further object of this invention is to provide a forearm splint system which achieves improved successful prevention of the development of carpal tunnel syndrome and other cumulative trauma disorders.

A further object of this invention is to provide a forearm splint system which achieves improved successful treatment and prevention of the development of carpal tunnel syndrome and other cumulative trauma disorders, which system does not immobilize the wrist, hand, fingers or thumb.

A further object of this invention is to provide a forearm splint system which achieves improved successful treatment and prevention of the development of carpal tunnel syndrome and other cumulative trauma disorders, which system can be worn comfortably during activities that are likely to contribute to developing symptoms.

A further object of this invention is to provide a forearm splint system which achieves improved successful treatment and prevention of the development of carpal tunnel syndrome and other cumulative trauma disorders, which system reduces pressure in the carpal tunnel by rotating the radius and ulna towards each other, thus reducing tension in the flexor retinaculum and transverse carpal ligament.

A further object of this invention is to provide a forearm splint system which achieves improved successful treatment and prevention of the development of carpal tunnel syndrome and other cumulative trauma disorders, which system does not protrude from the wearer's wrist and interfere with one's ability to function, nor pose a safety hazard due to potential entanglement with objects near the wearer's hand and wrist.

A further object of this invention is to provide a forearm splint system which achieves improved successful treatment and prevention of the development of carpal tunnel syndrome and other cumulative trauma disorders, which system does not require periodic adjustments by a physician or health care provider.

A further object of this invention is to provide a forearm splint system which achieves improved successful treatment and prevention of the development of carpal tunnel syndrome and other cumulative trauma disorders, which system can be readily applied and worn comfortably for extended periods of time.

BRIEF SUMMARY OF THE INVENTION

In general the present invention consists of a forearm splint system comprised of two curved, semi-rigid pieces of material which exteriorly cradle and rotate the distal radius and ulna. The exterior surface of both curved, semi-rigid pieces is covered by a wide band of limited stretch material such as Neoprene. The length of such band is limited so that as it is wrapped around the volar surface of the forearm and wrist it neither covers nor compresses the area of the carpal tunnel. The interior surface of both curved, semi-rigid pieces is covered by a cushion material or foam fabric so as to avoid discomfort against the wearer's skin. Affixed to the exterior surface of said band, along the radial-dorsal portion, is a D-ring. Affixed to the exterior surface of said band, along the ulnar-dorsal portion, is an adjustable tension strap.

The adjustable tensioning means is accomplished by passing said strap around the ulnar side of the forearm, across but not in direct contact with the skin of the volar surface of the forearm, towards the radial side of the forearm. Said strap is then passed through the D-ring, reversing direction and passed back towards the ulnar side of the forearm. Said strap is then drawn comfortably tight and secured to itself by complementary hook and loop material such as that sold under the trademark VELCRO. Said adjustable tensioning means allows the wearer to secure the splint system on the forearm and adjust the amount of pressure applied to the distal radius and ulna by said curved, semi-rigid pieces of material. This pressure serves to rotate and reposition the distal radius and ulna towards each other, thus reducing tension in the flexor retinaculum and transverse carpal ligament. This reduced tension results in decreased pressure within the carpal tunnel, improved sliding and gliding of the flexor tendons and therefore decreased compression of the median nerve.

BRIEF DESCRIPTION OF THE SEVERAL VIEWS OF THE DRAWING

A more thorough understanding and appreciation of the invention can be obtained by considering the following detailed description in conjunction with the accompanying drawings. For the purpose of illustrating the invention, there is shown in the drawings an embodiment which is presently preferred. It should be understood that the invention is not limited to the precise arrangement and instrumentalities shown in which.

DETAILED DESCRIPTION OF THE INVENTION

Figure 1:
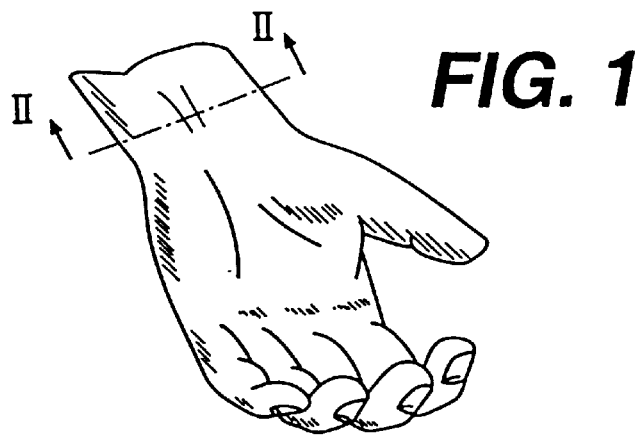
FIG. 1 is a perspective view of the palmar side of a left hand, wrist and forearm.

Referring now to the drawings, the best presently contemplated embodiment of the invention is described. The description is not intended in a limiting sense and is made solely with the intent of illustrating the general principles of the invention.

Figure 2:
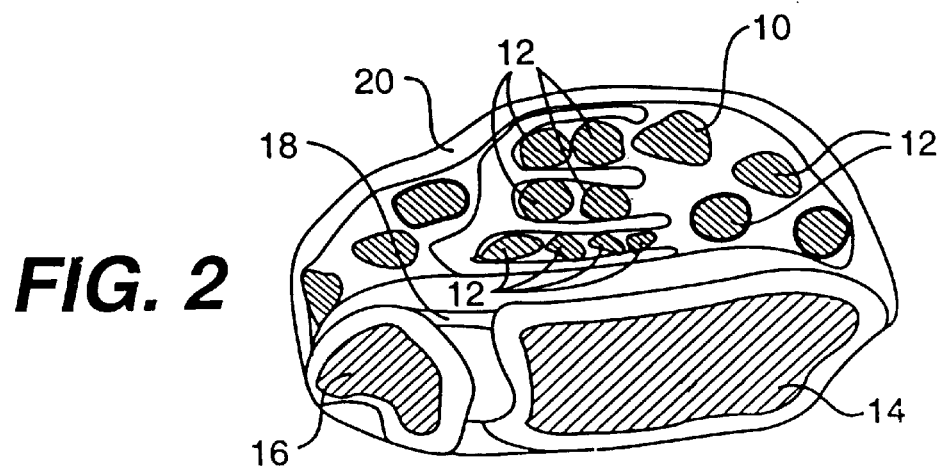
FIG. 2 is a cross-sectional view through the distal forearm along line II—II in FIG. 1 and looking in the direction of the arrows.

Referring now to the drawings in detail, where like numerals refer to like parts or elements. FIG. 1 depicts the distal forearm, wrist and hand of the left upper extremity. Line II transects the distal forearm at the level of the distal radioulnar joint just proximal to the radiocarpal joint. FIG. 2 depicts the contents of the carpal tunnel and related structures including the median nerve 10, the flexor tendons 12, the radius bone 14, the ulna bone 16, the interosseous ligament of the distal radioulnar joint 18, the flexor retinaculum and transverse carpal ligament 20.

Figure 3:
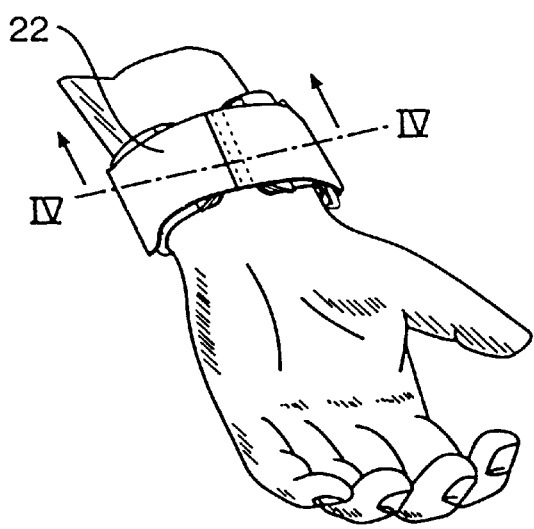
FIG. 3 is a perspective view of the palmar side of a left hand, wrist and forearm with the splint system in place on the wearer's forearm.
Figure 4:
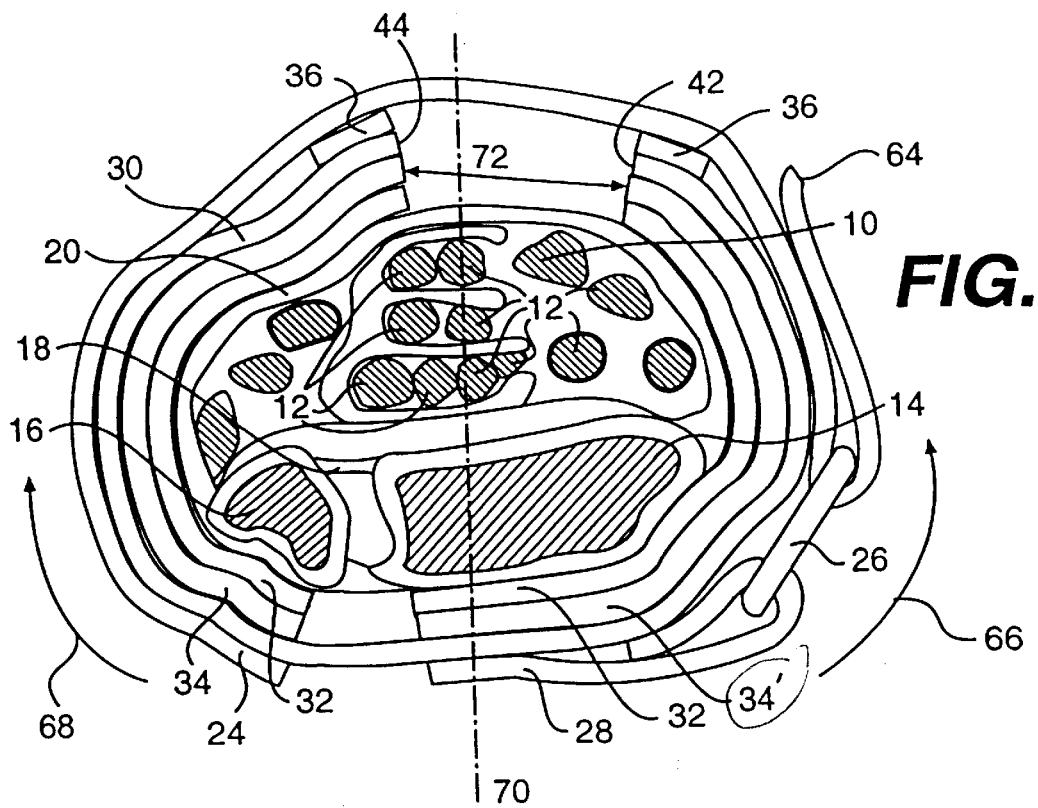
FIG. 4 is a cross-section view through the distal forearm along line IV—IV in FIG. 3 and looking in the direction of the arrows.

FIG. 3 depicts the splint system 22, in place on the wearer's forearm. Line IV transects the distal forearm and the splint system 22 at the level of the distal radioulnar joint just proximal to the radiocarpal joint. FIG. 4 depicts the contents of the carpal tunnel and related structures with the splint system 22 in place. Splint system 22 includes adjustable tension strap 24, D-ring 26, anchor loop for D-ring 28, a band of one way stretch material such as Neoprene or a more porous material if desired 30, cushion or foam fabric material of a porous nature 32, two curved, semi-rigid or repositioning members 34 and 34', and spacer pads of Neoprene or a more porous material if desired 36. The repositioning members may be composed of material selective from a group including thermoplastic resin, injecting molding plastic, fiberglass, resin, and metal. The cushion or foam fabric material may be selected from a group of materials including open cell foam, closed cell foam, leather, cotton fabric, or gel padding. The D-Ring may be composed of a material selective from a group including plastic, fiberglass, wood and metal.

Figure 5A:
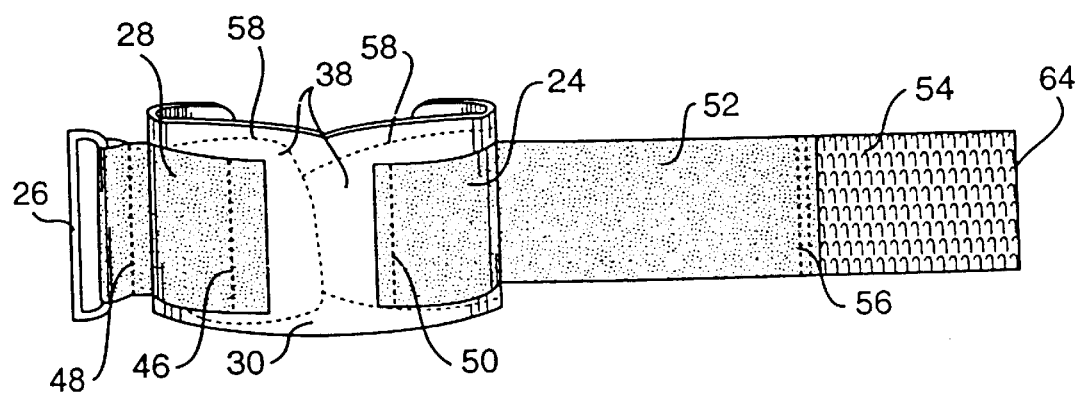
FIG. 5a is a plan view of the exterior surface of the splint system.
Figure 5B:
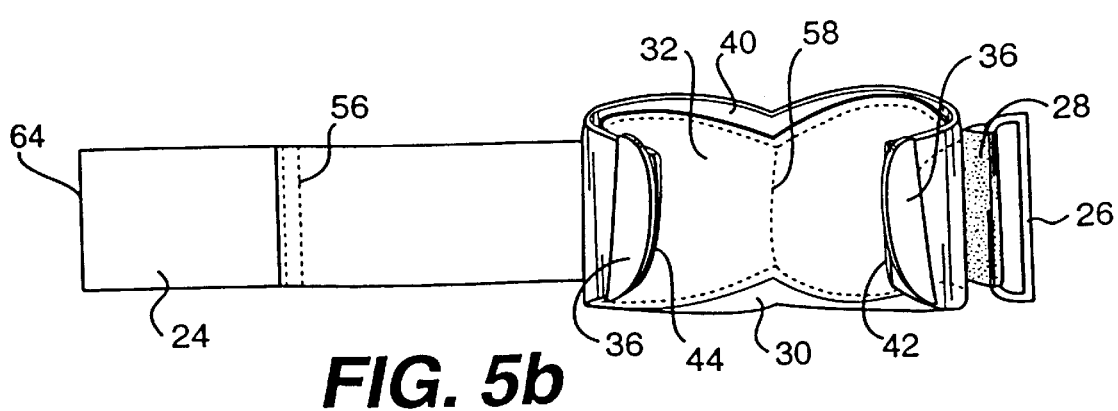
FIG. 5b is a plan view of the interior surface of the splint system.
Figure 5C:
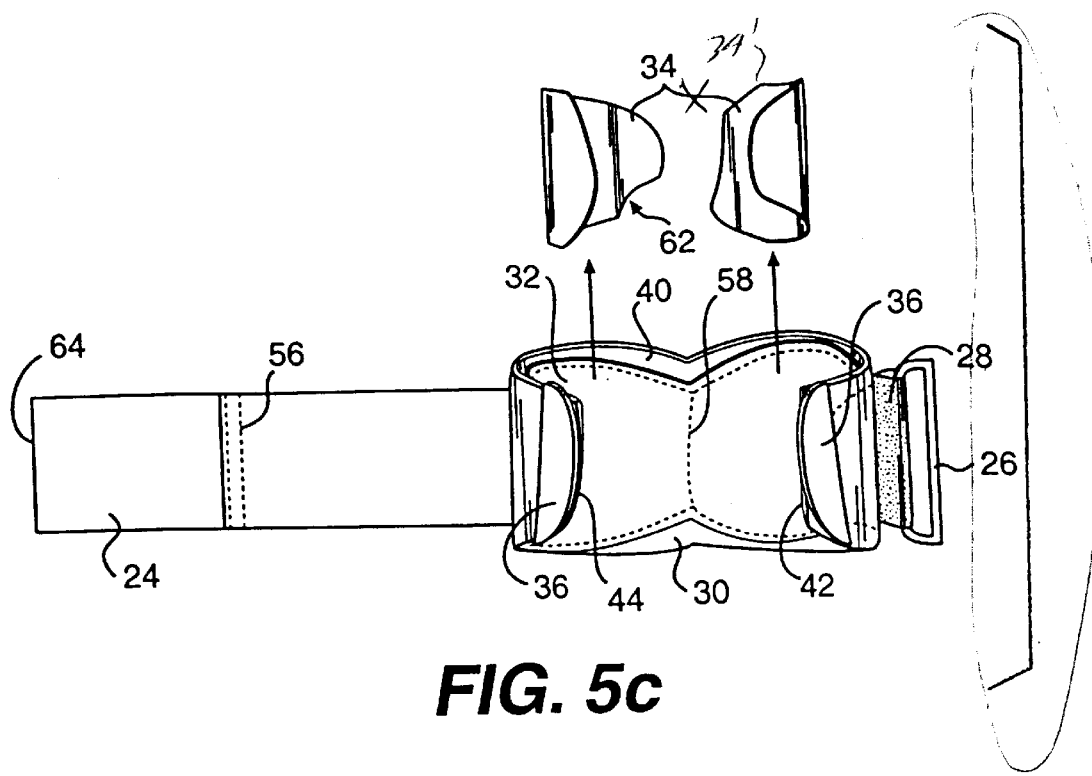
FIG. 5c is a plan, partially exploded view of the interior surface of the splint system.

Referring now to FIGS. 5a–c the band 30 consists of an exterior surface 38, an interior surface 40, a radial free end 42 and an ulnar free end 44. Attached to the exterior surface 38 on the radial side is an anchor loop 28 by stitching 46 or other such attachment means. Said loop 28 is composed of a non-stretch material such as nylon. Said loop 28 is completed by passing said non-stretch material through the D-ring 26 and back upon itself wherein it is affixed to itself by stitching 48 or other such attachment means. Attention should now be drawn to the radial free end 42 and the ulnar free end 44 of the band 30. Spacer pads 36 are attached to said ends 42, 44 on the exterior surface 38 by means of stitching, gluing, complementary hook and loop material such as that sold under the trademark VELCRO or other such attachment means. Attached to the exterior surface 38 on the ulnar side is the adjustable tension strap 24. Said strap 24 is attached to said band 30 by means of stitching 50 or other such attachment means. Said strap 24 is composed of a non-stretch material such as nylon and has a loop portion 52 and a complementary hook portion 54. The loop portion 52 and the hook portion 54 are joined together to form one continuous piece of material by stitching 56 or other such attachment means. The two curved, semi-rigid pieces of material 34,34' and cushion or foam fabric 32 are attached to the interior surface 40 of the band 30 by stitching 58 or other such attachment means. Said cushion or foam fabric 32 prevents excessive pressure against the wearer's skin therefore improving comfort. Also being of a porous nature it allows moisture, ie. perspiration to evaporate, further enhancing comfort.

Figure 6:
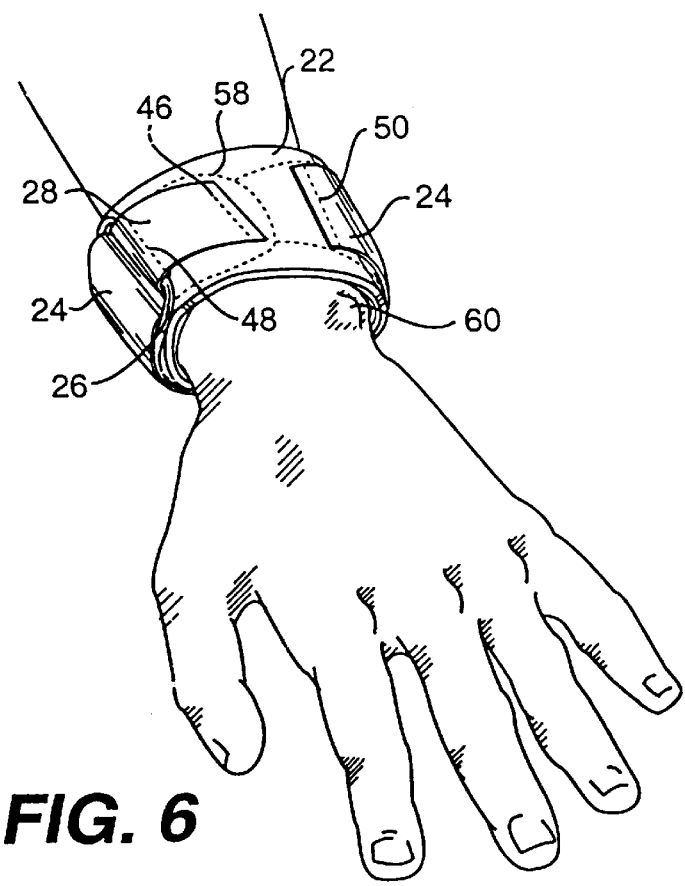
FIG. 6 is an enlarged perspective view of the dorsal side of a left hand, wrist and forearm with the splint system in place on the wearer's forearm.

Referring now to FIGS. 5c & 6, and specifically the two curved, semi-rigid pieces of material 34,34', note they are curved to conform generally to the shape of a wearer's forearm. This prevents gaps between the splint system 22 and the wearer's skin, reducing any tendency for the invention to roll or slide upon the wearer's forearm during activities requiring manual dexterity of the hand, thereby reducing friction. This further enhances the comfort of wearing said splint system 22. This also prevents protrusion of the splint system 22 and potential entanglement in objects near the wearer's wrist and hand. Furthermore, comfort is enhanced by avoiding excessive pressure over the ulnar styloid process 60 which is often a source of irritation with other types of splints. This is achieved by removing the curved corner at arrow 62, creating a recessed portion on said curved, semi-rigid piece of material 34.

Donning the splint system 22 is achieved much like one would don a wristwatch. The wearer would place their left forearm, wrist and hand in the splint system 22 as it is depicted in FIG. 5b. Thus the D-ring 26 would be on the radial side and the adjustable tension strap 24 would be on the ulnar side. The free end 64 of said strap 24 would then be pulled across the volar aspect of the forearm and wrist, intermitted through the D-ring 26, pulled back across itself and secured by the complementary hook portion 54 and loop portion 52. It will be appreciated that tightening the strap 24 is infinitely adjustable to accommodate a variety of individuals with different size forearms and requiring different amounts of rotation and repositioning of the distal radius and ulna. Furthermore, the length of band 30 is of such length that when wrapped around the wearer's forearm the radial free end 42 and the ulnar free end 44 do not come in contact with each other. This creates an open tubular shape when worn in the manner described. Said opening 72 would be aligned with the skin over the area of the carpal tunnel. Attention is now drawn to the spacer pads 36. It will be appreciated in FIG. 4 that as the adjustable tension strap 24 is drawn tight and secured, the splint system 22 does not exteriorly compress the carpal tunnel and its' contents.

The tension imparted by said adjustable tension strap 24 and the anchor loop 28 cause the two curved, semi-rigid pieces of material 34 to rotate in the directions depicted by arrows 66 and 68 in FIG. 4. This rotation of said curved, semi-rigid pieces of material 34,34' causes a rotation and repositioning of the distal radius 14 and ulna 16 without significantly compressing the distal radioulnar joint, its' associated cartilage and the closely related triangular fibrocartilage complex. This rotation and repositioning decreases the tension in the flexor retinaculum and transverse carpal ligament 20. These changes result in an increased diameter of the carpal tunnel along line 70. This provides more space for the flexor tendons 12 and the median nerve 10. This in and of itself will lead to decreased compression of the median nerve 10 and relief of carpal tunnel syndrome symptoms. Additionally the flexor tendons 12 will be provided improved frictionless gliding and sliding which will reduce inflammatory changes, that is thickening and swelling of said tendons 12 and their respective sheaths. This will further relieve the symptoms of carpal tunnel syndrome and cumulative trauma disorders.

Having thus described the invention it will be understood that numerous modifications and adaptations thereof will be readily apparent to those skilled in the art without departing from the spirit and the scope of the present invention. The length of the band 30 could be increased to comfortably fit the forearm of larger wearers or be somewhat shortened to comfortably fit the forearm of smaller wearers. The configuration may be reversed to accommodate the right forearm of a wearer. It is understood that instead of complementary hook and loop material such as that sold under the trademark VELCRO, fastening means could be snaps, buckles, hooks or laces and not depart from the true spirit of the present invention. Additionally the material of the band 30 could be any natural or synthetic material that offers one way stretch characteristics. The splint system 22 and its' components can be personalized in many ways. For instance, the exterior surface 38 can be decorated with printing, logos, embroidery, stenciling, painting, dyeing and/or plastic, leather, fabric or metal ornamentation. The exterior surface 38 can also be modified to attach a watch, timer, pager or other small portable appliance. It is intended that the claims herein appended will cover all such modifications and embodiments as fall within the true spirit and scope of the present invention.

What I claim as new and desire to secure by Letters Patent of the United States is:

1. A splint system for the treatment and prevention of carpal tunnel syndrome and other cumulative trauma disorders comprised of:
   a) repositioning means provided by two curved, semi-rigid pieces of material having an interior surface and an exterior surface and being dimensioned and oriented to exteriorly cradle the distal radius and ulna of a human being,
   b) cushioning means applied to the interior surface of said curved, semi-rigid pieces of material,
   c) a band of limited stretch material applied to the exterior surface of said curved, semi-rigid pieces of material, having two free ends, a proximal edge, a distal edge, an interior surface and an exterior surface and having a predetermined maximum length so that when wrapped around the forearm of a human being the two free ends do not contact each other,
   d) tensioning means provided by a strap of non-stretch material, narrower in width than said band, applied to the exterior surface of said band, having one free end and one fixed end, and having sufficient length to pass around the volar surface of the forearm of a human being, pass through an anchoring means, reversing direction and pass back across itself and be secured,
   e) securing means for said tensioning means allowing said tensioning means to be infinitely adjustable thus applying pressure to said repositioning means, said pressure causing the distal radius and ulna to rotate towards each other resulting in decreased tension in the flexor retinaculum and transverse carpal ligament, widening of the carpal tunnel, decreased compression of the median nerve, and improved gliding and sliding of the flexor tendons without reducing the manual dexterity of the hand.

2. The apparatus of claim 1 wherein said repositioning means are composed of material selected from a group including thermoplastic resin, injection molded plastic, fiberglass resin and metal.

3. The apparatus of claim 2 wherein said repositioning means positioned over the distal ulna is provided with a recessed portion to prevent uncomfortable pressure over the ulnar styloid process.

4. The apparatus of claim 1 wherein the cushioning means are composed of material selected from a group including open cell foam, closed cell foam, leather, cotton fabric or gel padding.

5. The apparatus of claim 1 wherein the securing means includes first and second mating portions of a hook and loop material carried of said tensioning means.

6. The apparatus of claim 1 wherein the anchoring means includes a D-ring affixed to the exterior surface of said band.

7. The apparatus of claim 6 wherein the D-ring is composed of material selected from a group consisting of plastic, fiberglass, wood and metal.

8. A method of treatment and prevention of carpal tunnel syndrome and other cumulative trauma disorders through decreasing tension in the flexor retinaculum and transverse carpal ligament, widening the carpal tunnel, decreasing compression of the median nerve, and improving gliding and sliding of the flexor tendons by rotating and repositioning the distal radius and ulna towards each other without reducing manual dexterity of the hand comprising the steps of:
   a) providing two curved repositioning members wherein one is dimensioned to cradle a person's forearm along the distal radius and the other is dimensioned to cradle a person's forearm along the distal ulna;
   b) positioning the two curved repositioning members in generally opposing relationship to the forearm along the distal radius and ulna;
   c) thereafter applying tensioning pressure to said two curved repositioning members to thereby urge the two repositioning members towards one another to thereby cause the distal radius and ulna to rotate towards one another without applying compression pressure to the area of the person's carpal tunnel, and
   d) thereafter securing the two repositioning members in place relative to the forearm.

9. The method of claim 8 including the additional step of placing cushioning material between the repositioning members and the forearm of the person.

10. A splint system for the treatment and prevention of carpal tunnel syndrome and other cumulative trauma disorders comprising:
    a) first and second repositioning means formed of generally semi-rigid material having inner surfaces which are concave and dimensioned and orientated to exteriorly cradle the distal radius and ulna of a human being,
    b) cushioning means along the inner surface of each said first and second repositioning means,
    c) a band of stretch material extending along an exterior of each said first and second repositioning means and having two free ends spaced from one another so that when wrapped around the forearm of a human being the two free ends are spaced from one another,
    d) tension means applied to an exterior surface of said band and having a free end having sufficient length to pass around the volar surface of the forearm of a human being and apply force on each of said first and second repositioning means so that said first and second repositioning means provide force adapted to cause the distal radius and ulna to rotate towards each other; and
    e) means for securing said tensioning means so as to continue to provide force on said first and second repositioning means so that said first and second repositioning means continue to provide force adapted to cause the distal radius, and ulna to rotate towards each other.

11. The splint system of claim 10 in which said first repositioning means includes a recessed corner portion so as to prevent pressure on the ulnar styloid process when in use.

12. The splint system of claim 10 including spacer means secured to each of said free ends of said band for spacing said tensioning means outwardly relative thereto.

* * * * *